United States Patent
Von Deak (10) Patent No.: US 12,064,749 B2
(45) Date of Patent: *Aug. 20, 2024

(54) HIGH GEOMETRIC SURFACE AREA CATALYSTS FOR VINYL ACETATE MONOMER PRODUCTION

(71) Applicant: BASF Corporation, Florham Park, NJ (US)

(72) Inventor: Dieter G. Von Deak, Hazlet, NJ (US)

(73) Assignee: BASF Corporation, Florham Park, NJ (US)

(*) Notice: Subject to any disclaimer, the term of this patent is extended or adjusted under 35 U.S.C. 154(b) by 254 days.

This patent is subject to a terminal disclaimer.

(21) Appl. No.: 17/092,065

(22) Filed: Nov. 6, 2020

(65) Prior Publication Data
US 2021/0069679 A1    Mar. 11, 2021

Related U.S. Application Data

(63) Continuation of application No. 16/708,966, filed on Dec. 10, 2019, now Pat. No. 10,864,500, which is a
(Continued)

(51) Int. Cl.
*B01J 23/52* (2006.01)
*B01J 31/02* (2006.01)
(Continued)

(52) U.S. Cl.
CPC .............. *B01J 23/52* (2013.01); *B01J 31/02* (2013.01); *B01J 31/0205* (2013.01); *B01J 31/04* (2013.01);
(Continued)

(58) Field of Classification Search
None
See application file for complete search history.

(56) References Cited

U.S. PATENT DOCUMENTS 3,284,851 A    11/1966    Zernay
3,857,780 A    12/1974    Gustafson
(Continued)

FOREIGN PATENT DOCUMENTS

CN    1345632 A    4/2002
CN    1513600 A    7/2004
(Continued)

OTHER PUBLICATIONS

Dorai et al., Packing fixed bed reactors with cylinders: Influence of particle length distribution, Procedia Engineering, 2012, 1335-1345 (Year: 2012).*
(Continued)

*Primary Examiner* — Coris Fung
*Assistant Examiner* — Keling Zhang
(74) *Attorney, Agent, or Firm* — LOWENSTEIN SANDLER LLP (57) ABSTRACT

A catalyst includes a support, where the support includes an external surface, about 60 wt % to about 99 wt % silica, and about 1.0 wt % to about 5.0 wt % alumina. A catalytic layer is disposed within the support adjacent to the external surface, where the catalytic layer further includes Pd, Au, and potassium acetate (KOAc). In the catalyst, (a) the KOAc is from about 60 kg/m$^3$ to about 150 kg/m$^3$ of the catalyst; or (b) the catalytic layer has an average thickness from about 50 µm to about 150 µm; or (c) both (a) and (b). The catalyst also possesses a Brunauer-Emmett-Teller surface area of about 130 m$^2$/g to about 300 m$^2$/g and a geometric surface area per packed bed volume from about 550 m$^2$/m$^3$ to about 1500 m$^2$/m$^3$. The catalyst is highly active for the synthesis of vinyl acetate monomer and exhibits a high selectivity for vinyl acetate monomer.

15 Claims, 4 Drawing Sheets

Related U.S. Application Data continuation of application No. 15/745,859, filed as application No. PCT/US2016/043387 on Jul. 21, 2016, now Pat. No. 10,525,448.

(60) Provisional application No. 62/195,499, filed on Jul. 22, 2015.

(51) Int. Cl.
*B01J 31/04* (2006.01)
*B01J 35/40* (2024.01)
*B01J 35/61* (2024.01)
*B01J 37/02* (2006.01)
*B01J 37/16* (2006.01)
*C07C 67/055* (2006.01)
*B01J 21/12* (2006.01)
*B01J 23/44* (2006.01)
*B01J 35/31* (2024.01)
*B01J 35/50* (2024.01)

(52) U.S. Cl.
CPC .............. *B01J 35/40* (2024.01); *B01J 35/615* (2024.01); *B01J 35/617* (2024.01); *B01J 35/618* (2024.01); *B01J 37/02* (2013.01); *B01J 37/0201* (2013.01); *B01J 37/024* (2013.01); *B01J 37/16* (2013.01); *C07C 67/055* (2013.01); *B01J 21/12* (2013.01); *B01J 23/44* (2013.01); *B01J 31/0274* (2013.01); *B01J 35/31* (2024.01); *B01J 35/50* (2024.01); *B01J 2523/00* (2013.01)

(56) References Cited

U.S. PATENT DOCUMENTS

| | | | |
|---|---|---|---|
| 3,920,578 A | 11/1975 | Yates | |
| 4,142,994 A | 3/1979 | Alafandi | |
| 4,330,519 A | 5/1982 | Takahashi et al. | |
| 4,366,093 A | 12/1982 | Shiozaki et al. | |
| 4,441,990 A | 4/1984 | Huang | |
| 4,510,262 A | 4/1985 | Kim et al. | |
| 4,510,263 A * | 4/1985 | Pereira | C10G 45/08 502/527.16 |
| 4,511,671 A | 4/1985 | Saito et al. | |
| 4,541,996 A | 9/1985 | Pereira et al. | |
| 4,631,267 A | 12/1986 | Lachman et al. | |
| 4,631,268 A | 12/1986 | Lachman et al. | |
| 4,673,664 A | 6/1987 | Bambrick | |
| 4,731,352 A | 3/1988 | Sekido et al. | |
| 4,772,579 A | 9/1988 | Thistlethwaite et al. | |
| 4,780,446 A | 10/1988 | Nozemack et al. | |
| 4,829,043 A | 5/1989 | Boehning et al. | |
| 4,868,150 A | 9/1989 | Spooner et al. | |
| 4,937,394 A | 6/1990 | Dreibelbis | |
| 4,950,628 A | 8/1990 | Landon et al. | |
| 5,004,709 A | 4/1991 | Stranford et al. | |
| 5,034,369 A | 7/1991 | Hebrard et al. | |
| 5,072,052 A | 12/1991 | Boeck et al. | |
| 5,116,659 A | 5/1992 | Glatzle et al. | |
| 5,166,120 A | 11/1992 | Deller et al. | |
| 5,326,915 A | 7/1994 | Viola et al. | |
| 5,371,277 A | 12/1994 | Matsumoto et al. | |
| 5,466,652 A | 11/1995 | Paparizos et al. | |
| 5,507,980 A | 4/1996 | Kelkar et al. | |
| 5,610,116 A | 3/1997 | Werdecker et al. | |
| 5,633,066 A | 5/1997 | Lipp et al. | |
| 5,808,136 A | 9/1998 | Tacke et al. | |
| 5,861,353 A | 1/1999 | Viola et al. | |
| 5,905,054 A | 5/1999 | Cavalli et al. | |
| 5,935,896 A | 8/1999 | Dupuis et al. | |
| 5,935,897 A | 8/1999 | Trubenbach et al. | |
| 6,166,280 A | 12/2000 | Rubin et al. | |
| 6,258,328 B1 | 7/2001 | Torkkell et al. | |
| 6,316,383 B1 | 11/2001 | Tacke et al. | |
| 6,593,269 B1 | 7/2003 | Rubini et al. | |
| 6,617,270 B1 | 9/2003 | Austin et al. | |
| 6,679,986 B1 | 1/2004 | Da Silva et al. | |
| 6,712,953 B1 | 3/2004 | Kasztelan et al. | |
| 6,794,332 B2 | 9/2004 | Khanmamedova et al. | |
| 7,320,778 B2 | 1/2008 | Whittenberger | |
| 7,799,730 B2 | 9/2010 | Ringer et al. | |
| 7,811,963 B2 | 10/2010 | Klaver et al. | |
| 8,048,820 B2 | 11/2011 | Brandstadter et al. | |
| 8,216,964 B2 | 7/2012 | Wang et al. | |
| 2001/0023840 A1 | 9/2001 | Harle et al. | |
| 2001/0029235 A1 | 10/2001 | Walsdorff et al. | |
| 2002/0045540 A1 | 4/2002 | Bartholdy | |
| 2002/0045541 A1 | 4/2002 | Koike et al. | |
| 2002/0179887 A1 | 12/2002 | Zeng et al. | |
| 2002/0198429 A1 | 12/2002 | Ramani et al. | |
| 2003/0038059 A1 | 2/2003 | Zanibelli et al. | |
| 2003/0113538 A1 | 6/2003 | Tom et al. | |
| 2003/0162649 A1 | 8/2003 | Basso et al. | |
| 2004/0052714 A1 | 3/2004 | Rojas et al. | |
| 2004/0133052 A1 | 7/2004 | Petrolli et al. | |
| 2004/0185244 A1 | 9/2004 | Van Hasselt et al. | |
| 2005/0025690 A1 | 2/2005 | Fukuda et al. | |
| 2005/0047951 A1 | 3/2005 | Gronquist et al. | |
| 2005/0075246 A1 | 4/2005 | Marsella et al. | |
| 2005/0077496 A1 | 4/2005 | Shimizu et al. | |
| 2005/0130837 A1 | 6/2005 | Hoek et al. | |
| 2005/0232853 A1 | 10/2005 | Evans et al. | |
| 2006/0178769 A1 | 8/2006 | Brew et al. | |
| 2007/0166439 A1 | 7/2007 | Soe et al. | |
| 2007/0297956 A1 | 12/2007 | Repasky et al. | |
| 2008/0023863 A1 | 1/2008 | Lee et al. | |
| 2008/0096761 A1 | 4/2008 | Mihan et al. | |
| 2008/0182049 A1 | 7/2008 | Tsuchimoto et al. | |
| 2008/0202336 A1 | 8/2008 | Hofer et al. | |
| 2008/0262115 A1 | 10/2008 | Calis et al. | |
| 2008/0287290 A1 | 11/2008 | Wang et al. | |
| 2009/0275788 A1 | 11/2009 | Bedard et al. | |
| 2010/0025628 A1 | 2/2010 | Bedard et al. | |
| 2010/0041929 A1 | 2/2010 | Bedard et al. | |
| 2010/0056839 A1 | 3/2010 | Ramachandran et al. | |
| 2010/0069659 A1 | 3/2010 | Raichle et al. | |
| 2010/0069660 A1 | 3/2010 | Raichle et al. | |
| 2010/0094069 A1 | 4/2010 | Bedard et al. | |
| 2010/0152505 A1 | 6/2010 | Orsenigo et al. | |
| 2010/0249480 A1 | 9/2010 | Nicholas et al. | |
| 2010/0279846 A1 | 11/2010 | Dahar et al. | |
| 2010/0331571 A1 | 12/2010 | Saito et al. | |
| 2011/0054196 A1 | 3/2011 | Hirota et al. | |
| 2011/0073522 A1 | 3/2011 | Bonduelle et al. | |
| 2011/0124936 A1 | 5/2011 | Cabiac et al. | |
| 2011/0172088 A1 | 7/2011 | Bedard et al. | |
| 2011/0172482 A1 | 7/2011 | Cabiac et al. | |
| 2011/0210473 A1 | 9/2011 | Duroe | |
| 2012/0034688 A1 | 2/2012 | Griffin | |
| 2012/0065055 A1 | 3/2012 | Jiang et al. | |
| 2012/0098156 A1 | 4/2012 | Ausen et al. | |
| 2012/0108832 A1 | 5/2012 | Chen et al. | |
| 2012/0115967 A1 | 5/2012 | Bezemer et al. | |
| 2013/0006002 A1 | 1/2013 | Rizkalla | |
| 2013/0112605 A1 | 5/2013 | Wyndham et al. | |
| 2013/0172603 A1 | 7/2013 | Hagemeyer et al. | |
| 2013/0338378 A1 | 12/2013 | Reitzmann et al. | |
| 2014/0039218 A1 | 2/2014 | Dellamorte et al. | |

FOREIGN PATENT DOCUMENTS

| | | |
|---|---|---|
| CN | 101168440 A | 4/2008 |
| CN | 101224409 A | 7/2008 |
| CN | 101376830 A | 3/2009 |
| CN | 101376832 A | 3/2009 |
| CN | 101433863 A | 5/2009 |
| CN | 101767790 A | 7/2010 |
| CN | 102309998 A | 1/2012 |
| CN | 102463142 A | 5/2012 |
| CN | 102485847 A | 6/2012 |
| CN | 202570186 | 12/2012 |
| DE | 35 39 195 A | 5/1986 |
| DE | 41 28 201 A1 | 3/1993 |

(56) References Cited

FOREIGN PATENT DOCUMENTS

| | | |
|---|---|---|
| DE | 41 42 902 A1 | 6/1993 |
| DE | 19519616 A1 | 12/1996 |
| DE | 10 2004 034 039 A1 | 2/2006 |
| DE | 10 2006 046 538 A1 | 4/2008 |
| DE | 10 2008 042 061 A1 | 3/2010 |
| DE | 10 2008 042 064 A1 | 3/2010 |
| DE | 10 2008 054 586 A1 | 6/2010 |
| EP | 0 139 80 A1 | 8/1980 |
| EP | 0 309 048 A | 3/1986 |
| EP | 0 178 426 A | 4/1986 |
| EP | 0 355 231 A | 2/1990 |
| EP | 0 428 223 A | 5/1991 |
| EP | 0 723 810 B1 | 7/1996 |
| EP | 0 732 146 A1 | 9/1996 |
| EP | 1 194 235 A1 | 4/2002 |
| FR | 2904783 A1 | 2/2008 |
| GB | 2 158 963 A | 11/1985 |
| JP | 57-171435 A | 10/1982 |
| JP | 63-137752 A | 6/1988 |
| JP | 06-199582 A | 7/1994 |
| JP | 11-236602 A | 8/1999 |
| JP | 2000-135437 A | 5/2000 |
| JP | 2001-253705 A | 9/2001 |
| JP | 2002-119855 A | 4/2002 |
| JP | 2003-210981 A | 7/2003 |
| JP | 2006-263635 A | 10/2006 |
| JP | 2009-190964 A | 8/2009 |
| JP | 2011-206727 A | 10/2011 |
| JP | 2012-091358 A | 5/2012 |
| JP | 2013-534471 A | 9/2013 |
| RU | 2446878 C1 | 4/2012 |
| SE | 9402883 A | 3/1996 |
| SU | 865792 B | 9/1981 |
| WO | WO-00/72966 A1 | 12/2000 |
| WO | WO-01/00323 A1 | 1/2001 |
| WO | WO-2005/065821 A1 | 7/2005 |
| WO | WO-2008/060965 A2 | 5/2008 |
| WO | WO-2008/060968 A2 | 5/2008 |
| WO | WO-2008/060971 A2 | 5/2008 |
| WO | WO-2008/060972 A2 | 5/2008 |
| WO | WO-2008/060974 A2 | 5/2008 |
| WO | WO-2008/060976 A2 | 5/2008 |
| WO | WO-2008/060985 A2 | 5/2008 |
| WO | WO-2008/060987 A2 | 5/2008 |
| WO | WO-2008/060993 A2 | 5/2008 |
| WO | WO-2008/060992 A3 | 7/2008 |
| WO | WO-2009/071863 A2 | 6/2009 |
| WO | WO-2010/076249 A1 | 7/2010 |
| WO | WO-2011/107764 A1 | 9/2011 |
| WO | WO-2012/032325 A1 | 3/2012 |
| WO | WO-2012/069481 A1 | 5/2012 |
| WO | WO-2014/008187 | 1/2014 |

OTHER PUBLICATIONS

Benenati et al., Void fraction distribution in beds of spheres, A.I.Ch.E. Journal, 8, 3, 1962 (Year: 1962).*

Extended European Search Report in EP Application No. 16828555.9, mailed on Dec. 13, 2018. (8 pages).

International Search Report and Written Opinion in International Application No. PCT/US2016/043387 mailed on Oct. 26, 2016 (19 pages).

Kyriopoulos, "Development of high performance vinyl acetate monomer (VAM) catalysts,"Technische Universitt Darmstadt, 2009, pp. I-V and 1-122.

Notice of Allowance in U.S. Appl. No. 15/745,859, mailed on Aug. 21, 2019.

Notice of Allowance in U.S. Appl. No. 16/708,966, mailed on Sep. 11, 2020.

* cited by examiner

HIGH GEOMETRIC SURFACE AREA CATALYSTS FOR VINYL ACETATE MONOMER PRODUCTION

CROSS-REFERENCE TO RELATED APPLICATIONS

This application is a continuation of U.S. patent application Ser. No. 16/708,966, filed on Dec. 10, 2019, which is a continuation of U.S. patent application Ser. No. 15/745,859, filed on Jan. 18, 2018 and now U.S. Pat. No. 10,525,448, which is a U.S. National Phase Application under 35 U.S.C. § 371 of International Application No. PCT/US2016/043387, filed on Jul. 21, 2016, which claims the benefit of U.S. Provisional Patent Application No. 62/195,499, filed on Jul. 22, 2015, the entire disclosures of which are incorporated herein by reference for any and all purposes.

FIELD

The present technology relates generally to the field of vinyl acetate monomer production. More specifically, the catalysts are highly active for the synthesis of vinyl acetate monomer and exhibit a high selectivity. The present technology also provides methods of making the catalysts and processes involving the catalysts.

BACKGROUND

The vinyl acetate monomer (VAM) is a compound represented by the following formula:

VAM is an important component in a wide variety of products, including polymers. VAM is also an important intermediate in coatings, textiles, paints, and other applications. For example, the polymer of VAM, polyvinyl acetate, is used in myriad applications including glues and adhesives.

SUMMARY

In an aspect, a catalyst is provided including a support that includes an external surface, about 60 wt % to about 99 wt % silica, about 1.0 wt % to about 5.0 wt % alumina, and a catalytic layer disposed within the support adjacent to the external surface, where the catalytic layer further includes Pd, Au, and potassium acetate (KOAc); a Brunauer-Emmett-Teller surface area of about 130 m$^2$/g to about 300 m$^2$/g; and a geometric surface area per packed bed volume (GSA/PBV) from about 550 m$^2$/m$^3$ to about 1500 m$^2$/m$^3$, where (a) the KOAc is from about 60 kg/m$^3$ to about 150 kg/m$^3$ of the catalyst; or (b) the catalytic layer has an average thickness from about 50 μm to about 150 μm, or (c) the KOAc is from about 60 kg/m$^3$ to about 150 kg/m$^3$ of the catalyst and the catalytic layer has an average thickness from about 50 μm to about 150 μm. In some embodiments, the KOAc may be from about 65 kg/m$^3$ to about 100 kg/m$^3$ of the catalyst. In any of the above embodiments, the catalytic layer may be from about 50 μm to about 550 μm thick.

In any of the above embodiments, the alumina may be from about 1.0 wt % to about 3.0 wt %. In any of the above embodiments, the Pd in the catalyst may be from about 3 g/L to about 15 g/L. In any of the above embodiments, the Au in the catalyst may be from about 0.9 g/L to about 7 g/L. In any of the above embodiments, the mass ratio of Pd to Au may be from about 3.5:1 to about 2.0:1. In any of the above embodiments, the void fraction of the catalyst may be from about 35% to about 55%. In any of the above embodiments, the catalyst may be in a shape including at least one of cylindrical, spherical, tubular, polylobular, ring, star, saddle, fluted, or ridged. In any of the above embodiments, it may be that with the exception of the catalytic layer, the support is substantially free of Pd, Au, and KOAc.

In an aspect, method of making any one of the previously described catalysts is provided. The method includes permeating a support material (which includes an external surface with Pd and Au) to provide a metal-containing layer disposed within the support material adjacent to the external surface. The support material includes about 60 wt % to about 99 wt % silica, and about 1.0 wt % to about 5.0 wt % alumina, and the metal-containing layer further includes Pd and Au.

In some embodiments, permeating the support material includes contacting the support material with a salt solution that includes a salt of Pd, a salt of Au, or a mixture thereof. In any of the above embodiments, it may be that subsequent to contacting with the salt solution, permeating the support material includes contacting the support material with a basic solution. In any of the above embodiments, it may be that the method further includes a washing step subsequent to the permeating step. In any of the above embodiments, it may be that the method further includes drying the support material subsequent to the permeating step. In any of the above embodiments, the drying subsequent to the permeating step may be conducted at a temperature from about 40° C. to about 250° C. In any of the above embodiments, the method may also include drying the support material subsequent to the washing step. In any of the above embodiments, the drying subsequent to the washing step may be conducted at a temperature from about 40° C. to about 250° C.

In any of the above embodiments, the method may further include exposing the metal-containing layer to a reducing agent. The exposing step may be conducted at a temperature from about 15° C. to about 500° C.

In any of the above embodiments, the method may further include impregnating the metal-containing layer with KOAc. The impregnating step may occur prior to the exposing step, or that the impregnating step may occur after the exposing step. In any of the above embodiments, the method may further include drying the support material subsequent to the impregnating step.

In an aspect, a process is provided that includes contacting a reactant gas with the catalyst of any one of the above embodiments to produce vinyl acetate monomer, where the reactant gas includes ethylene, acetic acid, and O$_2$.

DETAILED DESCRIPTION

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{15}$ are thus within the scope of the present technology. Procedures for inserting such labels into the compounds of the present technology will be readily apparent to those skilled in the art based on the disclosure herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

"Substantially free" as used herein will be understood by persons of ordinary skill in the art and will vary to some extent depending upon the context. If there are uses of the term which are not clear to persons of ordinary skill in the art, given the context in which it is used, "substantially free" will mean that the substance is at about 0.5 wt % or less.

Catalysts have been identified and are described herein, that, when used to produce vinyl acetate monomer ("VAM"), exhibit high catalytic activity and high selectivity in producing VAM. The catalysts include a support that includes an external surface, about 60 wt % to about 99 wt % silica, about 1.0 wt % to about 5.0 wt % alumina, and a catalytic layer disposed within the support adjacent to the external surface, where the catalytic layer further includes Pd, Au, and potassium acetate (KOAc). In the catalyst, (a) the KOAc is from about 60 kg/m³ to about 150 kg/m³ of the catalyst; or (b) the catalytic layer has an average thickness from about 50 μm to about 150 μm, or (c) the KOAc is from about 60 kg/m³ to about 150 kg/m³ of the catalyst and the catalytic layer has an average thickness from about 50 μm to about 150 μm. The catalyst exhibits a Brunauer-Emmett-Teller surface area of about 130 m²/g to about 300 m²/g and a geometric surface area per packed bed volume (GSA/PBV) from about 550 m²/m³ to about 1500 m²/m³. The catalyst may be an extrudate catalyst, a precipitate catalyst, or a sphere-like catalyst. In some embodiments, the catalyst is an extrudate catalyst. Formation of extrudate catalysts typically includes pushing a paste through a die with or without cutting to length. Extrudate catalysts may be formed with solid or hollow interiors; the exteriors of an extrudate catalyst may have cross-sectional shape including, but not limited to, cylindrical, tubular, polylobular, ring, star, a trilobe, a quadrilobe, a cloverleaf shape, saddle, fluted, ridged, a multi-pointed star, a fluted ring, a hallow cylinder, a cogwheel, a spoked wheel, a multi-hole pellet, or a monolith.

The support includes from about 60 wt % to about 99 wt % silica. In any embodiment herein, the support may include silica in an amount of about 60 wt %, about 62 wt %, about 64 wt %, about 66 wt %, about 68 wt %, about 70 wt %, about 75 wt %, about 80 wt %, about 85 wt %, about 90 wt %, about 95 wt %, about 98 wt %, about 99 wt %, or any range including and in between any two of these values. The support also includes alumina in an amount from about 1.0 wt % to about 5.0 wt %. The amount of alumina in the support may be about 1.0 wt %, about 1.2 wt %, about 1.4 wt %, about 1.6 wt %, about 1.8 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %, about 4.0 wt %, about 4.2 wt %, about 4.4 wt %, about 4.6 wt %, about 4.8 wt %, about 5.0 wt %, or any range including and in between any two of these values. For example, in any of the above embodiments, the alumina may be from about 1.0 wt % to about 3.0 wt %.

As noted above, the catalyst has a Brunauer-Emmett-Teller surface area ("BET surface area") from about 130 m²/g to about 300 m²/g. The BET surface area may be determined by several methods, including the method described in ASTM-D3663-03 (2008), incorporated herein by reference in its entirety for any and all purposes. The BET surface area may be about 130 m²/g, about 140 m²/g, about 150 m²/g, about 160 m²/g, about 170 m²/g, about 180 m²/g, about 190 m²/g, about 200 m²/g, about 210 m²/g, about 220 m²/g, about 230 m²/g, about 240 m²/g, about 250 m²/g, about 260 m²/g, about 270 m²/g, about 280 m²/g, about 290 m²/g, about 300 m²/g, or any range including and in between any two of these values. For example, in any of the above embodiments, the catalyst may have a BET surface area from about 200 m²/g to about 250 m²/g.

The GSA/PBV excludes surface area provided by macro, meso, and micro pores. While there are a variety of ways of determining GSA/PBV for the catalysts, certain examples are provided below.

Geometric Surface Area (GSA)

For spherical catalysts, the geometric surface area (GSA) of a spherical catalyst is essentially $4\pi(r)^2$, where "r" is the half of the diameter of the spherical catalyst.

Figure 1:
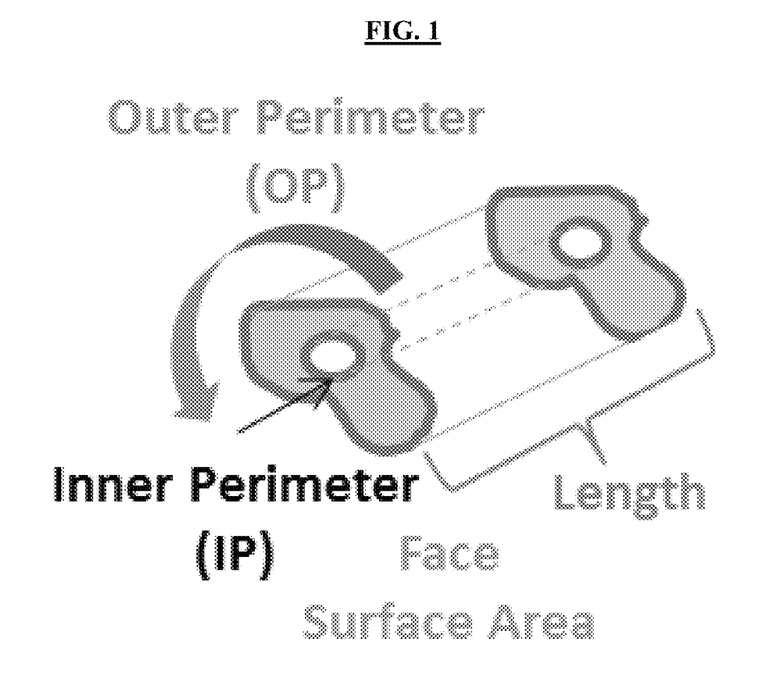
FIG. 1 illustrates measurement parameters of an extrudate catalyst used in an exemplary determination of the geometric surface area per packed bed volume of the extrudate catalyst.

For extrudate catalysts, the GSA may be assessed as follows. The outer perimeter (OP), inner perimeter (IP; when present), and face surface area (FSA) of the extrudate catalyst may be measured with a calibrated optical microscope. FIG. 1 illustrates the outer perimeter, inner perimeter, face surface area (shaded), and length dimensions. The length of the extrudate catalyst may be measured using a micrometer. Using these measurements, the geometric surface area of a single extrudate catalyst may be calculated as indicated in Equation 1.

$$GSA = 2*(FSA) + (IP)*Length + (OP)*Length \quad \text{Eq. 1}$$

While FIG. 1 illustrates and Equation 1 describes the GSA of a catalyst with one void through the catalyst (a "hole"), if there are multiple holes in the face surface then the area attributed for each hole will be accounted for when determining the GSA. For example, a catalyst with a first hole with a $IP_1$, and second hole with $IP_2$, and a third hole with $IP_3$ would have a GSA of $2*(FSA)+(IP_1)*Length+(IP_2)*Length+(IP_3)*Length+(OP)*Length$. Because extrudate catalysts are formed by passage through a regularly sized die plate, the face surface area for all extrudate catalysts of a certain type (e.g., shape) may be assumed constant. With a constant face surface area, the only parameter that may vary from one extrudate catalyst to another is the length. To overcome this, a representative length distribution may be utilized to determine the GSA.

Figure 2:
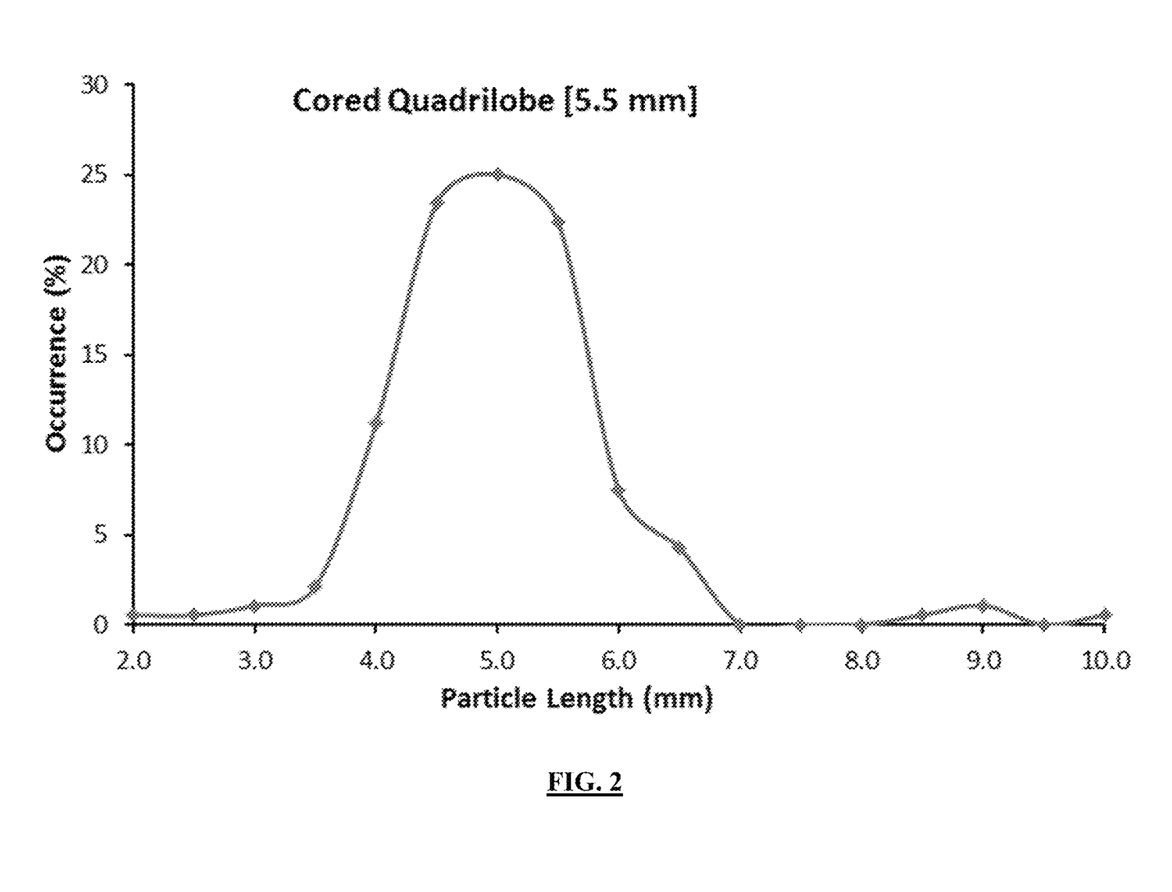
FIG. 2 illustrates a representative distribution of lengths for an extrudate catalyst obtained in an exemplary determination of the geometric surface area per packed bed volume of the extrudate catalyst.

To capture a representative length distribution, lengths may be determined for a number of extrudate catalysts greater than 100*(standard deviation in length). For example, if the standard deviation of measured lengths is 1.5, then 150 length measurements would be used to obtain a reasonably representative distribution. FIG. 2 provides an exemplary distribution curve for a cored quadrilobe extrudate catalyst according to the present technology with a diameter of about 5.5 mm at the longest point on the face surface. Using Equation 1, the geometric surface area of each of the extrudate catalysts of the distribution of extrudates may be calculated.

Geometric Surface Area Per Mass

Figure 3:
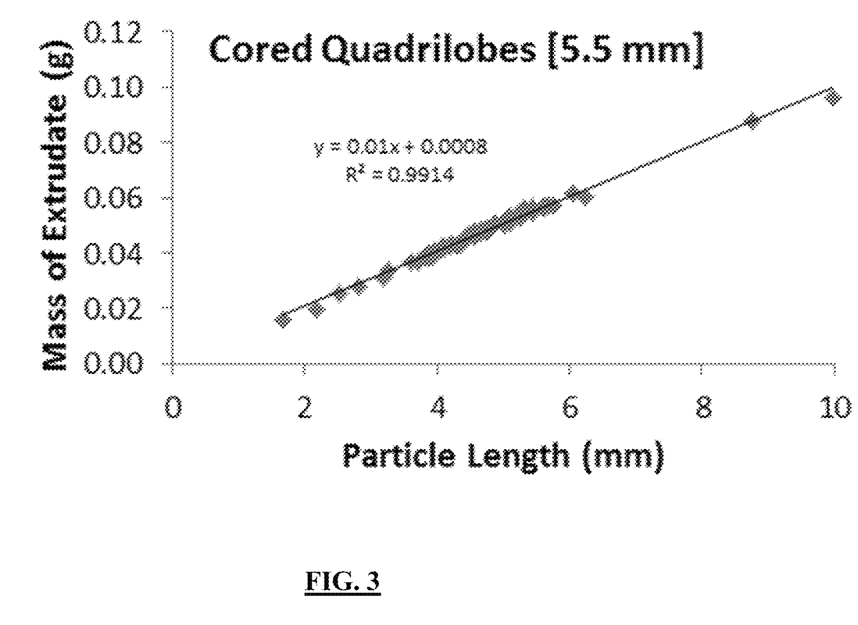
FIG. 3 provides the correlation of the distribution of lengths provided in FIG. 2 with the respective mass of the individual extrudate catalyst for which the particular length was obtained, utilized in an exemplary determination of the geometric surface area per packed bed volume of an extrudate catalyst.

To determine the geometric surface area per mass of catalyst from this ensemble of extrudate catalysts, a mass vs. length linear correlation may be assessed by measuring the mass and length of >50 extrudates. For extrudate catalyst, there is a strong correlation between the length and mass, as illustrated in FIG. 3 for the cored quadrilobe extrudate catalyst used in FIG. 2. Using the length distribution in FIG. 2 and the linear mass versus length correlation in FIG. 3, the geometric surface area per mass for the same distribution of 150 extrudate catalysts in FIG. 2 may be calculated, for example by using Equation 2. The "Mass of Particle$_i$" can be found from the linear mass versus length correlation in FIG. 3.

$$\sum_{i=1}^{>150} \frac{GSA_i}{\text{Mass of Particle}_i} = \frac{\text{External Surface}}{\text{Mass}} \quad \text{Eq. 2}$$

A similar procedure may be used to determine a representative geometric surface area per mass of a spherical catalyst. A representative value is achieved by using a large (at least greater than 50) ensemble of particles.

Obtaining the GSA/PBV

To obtain the GSA/PBV utilizing the geometric surface area per mass, the packed bed density of the catalyst type in question (e.g., a particular extrudate type, spherical catalyst, etc.) is measured. The packed bed density may be determined by a variety of methods, including, but not limited to, the method described in ASTM-D4164-82, incorporated herein by reference in its entirety for any and all purposes. Multiplying the geometric surface area per mass (in units of m²/g) with the packed bed density (the "Mass/Volume" in units of g/m³), cancels the mass units to provide the GSA/PBV, as shown in Equation 3.

$$\frac{\text{External Surface}}{\text{Mass}} * \frac{\text{Mass}}{\text{Volume}} = \frac{\text{External Surface}}{\text{Volume}} \quad \text{Eq. 3}$$

Using the exemplary analysis provided above reasonably describes the geometric surface area within a fixed packed bed volume of catalyst particles. However, it should be noted that other methods of determining GSA/PBV may be utilized.

For the catalysts, the GSA/PBV may be about 550 m²/m³, about 560 m²/m³, about 570 m²/m³, about 580 m²/m³, about 590 m²/m³, about 600 m²/m³, about 625 m²/m³, about 650 m²/m³, about 675 m²/m³, about 700 m²/m³, about 725 m²/m³, about 750 m²/m³, about 775 m²/m³, about 800 m²/m³, about 825 m²/m³, about 850 m²/m³, about 875 m²/m³, about 900 m²/m³, about 950 m²/m³, about 1000 m²/m³, about 1100 m²/m³, about 1200 m²/m³, about 1300 m²/m³, about 1400 m²/m³, about 1500 m²/m³, about 1000 m²/m³, or any range including and in between any two of these values. For example, the catalyst may have a GSA/PBV that is from about 600 m²/m³ to about 1500 m²/m³, or from about 800 m²/m³ to about 1300 m²/m³.

The KOAc is from about 60 kg/m³ to about 150 kg/m³ of the catalyst, and may be about 60 kg/m³, about 65 kg/m³, about 70 kg/m³, about 75 kg/m³, about 80 kg/m³, about 85 kg/m³, about 90 kg/m³, about 95 kg/m³, about 100 kg/m³, about 110 kg/m³, about 120 kg/m³, about 130 kg/m³, about 140 kg/m³, about 150 kg/m³, or any range including and in between any two of these values. For example, in any of the above embodiments, the KOAc may be from about 65 kg/m³ to about 100 kg/m³ of the catalyst.

Figure 4:
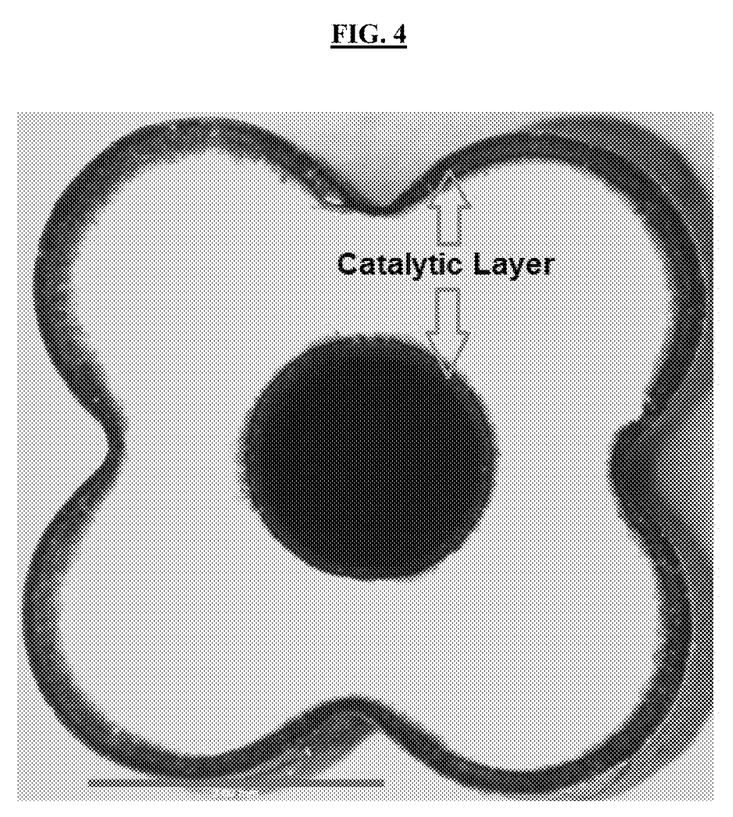
FIG. 4 provides a cross-section of a cored quadrilobe catalyst of the present technology where the dark bands adjacent to the support surface correspond to the catalytic layer, according to an embodiment of the present technology.

In any of the above embodiments, the catalytic layer may have an average thickness of about 50 µm to about 550 µm. Thus, the catalytic layer is disposed within the support adjacent to the external surface of the support and extends inward towards the interior of the support. The average thickness may be determined by using a calibrated optical microscope to measure the dark band on the outside of a cross-section of the catalyst particles. FIG. 4 illustrates a cross-section of a cored quadrilobe catalyst, where the dark bands on the periphery adjacent to the external surface correspond to the catalytic layer within the catalyst. While a variety of methods of determining the average thickness of the catalyst layer may be utilized, one approach includes measuring the catalytic layer thickness of ten (10) equidistant points of each external surface of the catalyst particle cross-section. For example, for the cored quadrilobe catalyst of FIG. 4 such measurements include measuring the catalytic layer thickness in the hole at the center as well as on the face. The average thickness of the catalytic layer of this cored quadrilobe catalyst may be determined by calculating the average of ten (10) equidistant catalytic layer thickness measurements from the cross section and ten (10) points from the extrudate face. For a spherical catalyst, the average thickness may be determined by calculating the average of ten (10) equidistant catalytic layer thickness measurements from the bisection of the spherical catalyst.

In the catalysts, the average thickness of the catalytic layer may be about 50 μm, about 55 μm, about 60 μm, about 65 μm, about 70 μm, about 75 μm, about 80 μm, about 85 μm, about 90 μm, about 95 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, or any range including and in between any two of these values.

The amount of Pd in the catalyst may be from about 3 g/L to about 15 g/L. The amount of Pd in the catalyst may be from about 3 g/L, about 4 g/L, about 5 g/L, about 6 g/L, about 7 g/L, about 8 g/L, about 9 g/L, about 10 g/L, about 11 g/L, about 12 g/L, about 13 g/L, about 14 g/L, about 15 g/L, or any range including and in between any two of these values. In any of the above embodiments, the Au in the catalyst may be from about 0.9 g/L to about 7.0 g/L; the amount of Au in the catalyst may be about 0.9 g/L, about 1.0 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, about 2.0 g/L, about 2.2 g/L, about 2.4 g/L, about 2.6 g/L, about 2.8 g/L, about 3.0 g/L, about 3.2 g/L, about 3.4 g/L, about 3.6 g/L, about 3.8 g/L, about 4.0 g/L, about 4.2 g/L, about 4.4 g/L, about 4.6 g/L, about 4.8 g/L, about 5.0 g/L, about 5.5 g/L, about 6.0 g/L, about 6.5 g/L, about 7.0 g/L, or any range including and in between any two of these values.

The mass ratio of Pd to Au may be from about 3.5:1 to about 2.0:1. The mass ratio of Pd to Au in any of the above embodiments may be about 3.5:1, about 3.4:1, about 3.3:1, about 3.2:1, about 3.1:1, about 3.0:1, about 2.9:1, about 2.8:1, about 2.7:1, about 2.6:1, about 2.5:1, about 2.4:1, about 2.3:1, about 2.2:1, about 2.1:1, about 2.0:1, or any range including and in between any two of these values.

The void fraction of the catalyst may be from about 35% to about 55%. Void fraction is the measure of the empty space in the catalyst and between individual catalysts when packed in a fixed bed, where the void fraction is the void volume in the packed fixed bed divided by the volume of the fixed bed. The void volume may be determined by a variety of methods, including, but not limited to, ASTM CCA11916, ASTM D6761-07, ASTM D5965-02, or ASTM C604-02. Thus, the void volume includes the empty space within the catalyst from features such as holes and depressions as well as between individual catalysts in a packed fixed bed. The void fraction of the catalyst may be about 35%, about 36%, about 37%, about 38%, about 39%, about 40%, about 42%, about 44%, about 46%, about 48%, about 50%, about 51%, about 52%, about 53%, about 54%, about 55%, or any range including and in between any two of these values.

The catalyst may be in a shape including, but not limited to, at least one of cylindrical, spherical, tubular, polylobular, ring, star, saddle, fluted, or ridged. Examples of such shapes include, but not limited to, a Raschig ring, a Pall ring, a Berl saddle, a Intalox saddle, a trilobes, a quadrilobes, a cloverleaf shape, a multi-lobed shape, a multi-pointed star, a fluted ring, a hallow cylinder, a cogwheel, a spoked wheel, a multi-hole pellets, or a monolith. In any of the above embodiments, the catalyst may have a diameter from about 2.0 millimeters ("mm") to about 9.0 mm. The diameter of the catalyst may be about 2.0 mm, about 2.1 mm, about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, about 4.2 mm, about 4.3 mm, about 4.4 mm, about 4.5 mm, about 4.6 mm, about 4.7 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, about 6.5 mm, about 6.6 mm, about 6.7 mm, about 6.8 mm, about 6.9 mm, about 7.0 mm, about 7.1 mm, about 7.2 mm, about 7.3 mm, about 7.4 mm, about 7.5 mm, about 7.6 mm, about 7.7 mm, about 7.8 mm, about 7.9 mm, about 8.0 mm, about 8.1 mm, about 8.2 mm, about 8.3 mm, about 8.4 mm, about 8.5 mm, about 8.6 mm, about 8.7 mm, about 8.8 mm, about 8.9 mm, about 9.0 mm, or any range including and in between any two of these values.

While the catalytic layer may include Pd, Au, and KOAc, the remaining support may be substantially free of Pd, Au, and KOAc. In any of the above embodiments, the amount of Pd in the support (not including the catalytic layer) may be less than about 0.4 wt %, less than about 0.3 wt %, less than about 0.2 wt %, less than about 0.1 wt %, or any range including and in between any two of these values. In any of the above embodiments, the amount of Au in the support (not including the catalytic layer) may be less than about 0.4 wt %, less than about 0.3 wt %, less than about 0.2 wt %, less than about 0.1 wt %, or any range including and in between any two of these values. In any of the above embodiments, the amount of KOAc in the support (not including the catalytic layer) may be less than about 0.4 wt %, less than about 0.3 wt %, less than about 0.2 wt %, less than about 0.1 wt %, or any range including and in between any two of these values.

In an aspect, method of making any one of the previously described catalysts is provided. The method includes permeating a support material (which includes an external surface with Pd and Au) to provide a metal-containing layer disposed within the support material adjacent to the external surface. The support material includes about 60 wt % to about 99 wt % silica, and about 1.0 wt % to about 5.0 wt % alumina, and the metal-containing layer further includes Pd and Au. The amount of silica, alumina, Pd, and Au may be any one or more of the previously discussed values.

In some embodiments, permeating the support material includes contacting the support material with a salt solution that includes a salt of Pd, a salt of Au, or a mixture thereof. In any of the above embodiments, the salt solution may include a chloride salt of Pd, a chloride salt of Au, or a mixture thereof. In any of the above embodiments, the solution may be an aqueous solution. In any of the above embodiments, the salt of Pd may be palladium (II) chloride, sodium palladium (II) chloride, palladium (II) nitrate, or a mixture of any two or more thereof. In any of the above embodiments, the salt of Au may be gold (III) chloride, tetrachloroauric (III) acid, or a mixture thereof.

In any of the above embodiments, subsequent to contacting with the salt solution, permeating the support material may include contacting the support material with a basic solution. The basic solution may be aqueous and may include sodium metasilicate. In any of the above embodiments, the method further include a washing step subsequent to the permeating step.

In any of the above embodiments, the method may further include drying the support material subsequent to the permeating step. In any of the above embodiments, drying subsequent to the permeating step may occur at a temperature from about 40° C. to about 250° C. Drying subsequent to the permeating step may occur at a temperature of about 40° C., about 50° C., about 60° C., about 70° C., about 80° C., about 90° C., about 100° C., about 125° C., about 150° C., about 175° C., about 200° C., about 225° C., about 250° C., or any range including and in between any two of these values. In any of the above embodiments, the drying subsequent to the permeating step may occur under vacuum. In any of the above embodiments, it may be that the method further includes drying the support material subsequent to the washing step. In any of the above embodiments, it may be that drying subsequent to the washing step occurs at a temperature from about 40° C. to about 250° C. Drying subsequent to the washing step may occur at a temperature of about 40° C., about 50° C., about 60° C., about 70° C., about 80° C., about 90° C., about 100° C., about 125° C., about 150° C., about 175° C., about 200° C., about 225° C., about 250° C., or any range including and in between any two of these values. In any of the above embodiments, the drying subsequent to the washing step may occur under vacuum. In any of the above embodiments, the drying subsequent to the washing step may occur under an inert atmosphere.

The method may further include exposing the metal-containing layer to a reducing agent. The reducing agent may include a reduction gas, where the reduction gas may include $H_2$. In any of the above embodiments, the reducing gas may include about 4% to about 100% $H_2$ on a molar basis. The reduction gas may include $H_2$ in an amount of about 4%, about 5%, about 6%, about 7%, about 8%, about 9%, about 10%, about 20%, about 30%, about 40%, about 50%, about 60%, about 70%, about 80%, about 90%, about 95%, about 98%, about 99%, about 100%, or any range including and in between any two of these values. The reducing gas may further include nitrogen gas, ethylene, or a mixture thereof. In embodiments where the reduction gas includes $H_2$ and nitrogen gas, the nitrogen gas and $H_2$ may be present in a ratio from about 5:1 to 1:1. The duration of the exposing step may be about 1 hour, about 2 hours, about 3 hours, about 4 hours, or any range including and in between any two of these values. The exposing step may occur at a temperature from about 15° C. to about 500° C.; thus, the exposing step may occur at a temperature of about 15° C., about 20° C., about 25° C., about 30° C., about 35° C., about 40° C., about 45° C., about 50° C., about 55° C., about 60° C., about 70° C., about 80° C., about 90° C., about 100° C., about 125° C., about 150° C., about 175° C., about 200° C., about 225° C., about 250° C., about 275° C., about 300° C., about 350° C., about 400° C., about 450° C., about 500° C., or any range including an in between any two of these values. For example, the exposing step may occur at a temperature from about 175° C. to about 500° C.

The method may further include impregnating the metal-containing layer with KOAc. The impregnating step may occur prior to the exposing step, or that the impregnating step occurs after the exposing step. The impregnating step may include contacting the metal containing layer with an aqueous solution of KOAc. In any of the above embodiments, the method may further include drying the support material subsequent to the impregnating step. Drying subsequent to the impregnating step may occur at a temperature of about 40° C., about 50° C., about 60° C., about 70° C., about 80° C., about 90° C., about 100° C., about 125° C., about 150° C., about 175° C., about 200° C., about 225° C., about 250° C., or any range including and in between any two of these values. In any of the above embodiments, the drying subsequent to the impregnating step may occur under vacuum. In any of the above embodiments, the drying subsequent to the impregnating step may occur under an inert atmosphere.

In an aspect, a process is provided that includes contacting a reactant gas with the catalyst of any one of the above embodiments to produce vinyl acetate monomer, where the reactant gas includes ethylene, acetic acid, and $O_2$. The contacting step may be contained within a fixed bed-type reactor that contains the catalyst. In such embodiments, it may be that the reactant gas flows through the fixed bed-type reactor containing the catalyst, where such flow accomplishes contacting the reactant gas with the catalyst.

However, the catalysts of the present technology may be used in other reactions, including (but not limited to) those involving an olefin, oxygen, and a carboxylic acid.

The examples herein are provided to illustrate advantages of the present technology and to further assist a person of ordinary skill in the art with preparing or using the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

While certain embodiments have been illustrated and described, a person with ordinary skill in the art, after reading the foregoing specification, can effect changes, substitutions of equivalents and other types of alterations to the compounds of the present technology. Each aspect and embodiment described above can also have included or incorporated therewith such variations or aspects as disclosed in regard to any or all of the other aspects and embodiments.

Composition of Exemplary Catalyst of Present Technology and a Comparative Catalyst.

The compositions and properties of two catalysts of the present technology (Catalyst 1 and Catalyst 2) and a Comparative Catalyst ("Comparative") are provided in Table 1 below. $SiO_2$ and $Al_2O_3$ were determined by X-ray florescence with a detection limit of ~0.1 wt %. Pd, Au, and K were determined by inductively coupled plasma atomic emission spectroscopy. All potassium measured was assumed to be from potassium acetate.

TABLE 1

|  | Comparative | Catalyst 1 | Catalyst 2 |
|---|---|---|---|
| $SiO_2$ (wt %) | 96.4 | 96.4 | 96.0 |
| $Al_2O_3$ (wt %) | 1.6 | 1.6 | 2.0 |
| KOAc (kg/m$^3$) | 40 | 40 | 61.7 |
| Pd (g/L) | 6.00 | 6.09 | 5.61 |
| Au (g/L) | 2.60 | 2.65 | 2.23 |
| BET surface area (m$^2$/g) | 255 | 255 | 230 |
| Geometric Surface Area (m$^2$/m$^3$) | 643 | 643 | 1042 |
| Void Fraction (%) | 39.8 | 39.8 | 51.5 |
| Packed ambient bulk density (g/cc) | 0.40 | 0.40 | 0.32 |
| Thickness of catalytic layer (μm) | 300 μm | 120 μm | 120 μm |
| Diameter | 5.8 mm | 5.8 mm | 6.6 mm |
| Shape | Spherical | Spherical | Polylobular, non-tubular |

N.D. = Not Detected

Improvements in Space-Time-Yield and Selectivity.

VAM production was evaluated in an isothermal fixed-bed reactor with silicon carbide filling the catalyst particle void space to eliminate gas channeling, where the results of FIGS. 1 and 2 are after 20 hours of operation at 150° C. The operating conditions for the reactor are provided in Table 2.

TABLE 2

| Temperature | 150° C. |
|---|---|
| Pressure | 8.27 bar |
| GHSV | 35,000 hr$^{-1}$ |
| Catalyst Bed Volume | 7.15 mL |

The reactant ee to the reactor was 79.24 mol % ethylene, 12.04 mol % acetic acid, 6.6 mol % $O_2$, and 2.11 mol % water. The space-time-yield and vinyl acetate selectivity are provided in Table 3 below.

TABLE 3

|  | Normalized Space-Time-Yield at 95% Vinyl Acetate Selectivity | Vinyl Acetate Selectivity (%) at 200 g VAM/[(g Pd)(hr)] |
|---|---|---|
| Comparative | 1 | 94.75 |
| Catalyst 1 | 1.25 | 95.59 |
| Catalyst 2 | 1.44 | 95.82 |

The space-time-yield is calculated to correct for differences in metal loading between the catalysts and was normalized with respect to the Comparative Catalyst. As shown in Table 3, Catalysts 1 and 2 are significantly more active catalysts than the Comparative Catalyst, where Catalyst 2 is more active than Catalyst 1. In addition, Catalysts 1 and 2 provide a significantly greater selectivity for vinyl acetate.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology includes, but is not limited to, the following lettered paragraphs:

A. A catalyst comprising:
    a support comprising:
        an external surface;
        about 60 wt % to about 99 wt % silica; and
        about 1.0 wt % to about 5.0 wt % alumina;
    a catalytic layer disposed within the support adjacent to the external surface, where the catalytic layer further comprises Pd, Au, and potassium acetate (KOAc);
    a Brunauer-Emmett-Teller surface area of about 130 m$^2$/g to about 300 m$^2$/g; and
    a geometric surface area per packed bed volume from about 550 m$^2$/m$^3$ to about 1500 m$^2$/m$^3$;
    wherein (a) the KOAc is from about 60 kg/m³ to about 150 kg/m³ of the catalyst; or
(b) the catalytic layer has an average thickness from about 50 µm to about 150 µm, or
(c) the KOAc is from about 60 kg/m³ to about 150 kg/m³ of the catalyst and the catalytic layer has an average thickness from about 50 µm to about 150 µm.

B. The catalyst of Paragraph A, wherein the KOAc is from about 65 kg/m³ to about 100 kg/m³ of the catalyst.
C. The catalyst of Paragraph A or B, wherein the catalytic layer has an average thickness from about 50 µm to about 550 µm.
D. The catalyst of any one of Paragraphs A-C, wherein the catalytic layer has an average thickness from about 100 µm to about 400 µm.
E. The catalyst of any one of Paragraphs A-D, wherein the catalytic layer has an average thickness from about 100 µm to about 200 µm.
F. The catalyst of any one of Paragraphs A-E, wherein the alumina is from about 1.0 wt % to about 3.0 wt %.
G. The catalyst of any one of Paragraphs A-F, wherein the Pd in the catalyst is from about 3 g/L to about 15 g/L.
H. The catalyst of any one of Paragraphs A-G, wherein the Au in the catalyst is from about 0.9 g/L to about 7.0 g/L.
I. The catalyst of any one of Paragraphs A-H, wherein the mass ratio of Pd to Au is from about 3.5:1 to about 2.0:1.
J. The catalyst of any one of Paragraphs A-I, wherein the Brunauer-Emmett-Teller surface area of the catalyst is from about 200 m²/g to about 250 m²/g.
K. The catalyst of any one of Paragraphs A-J, wherein the geometric surface area per packed bed volume of the catalyst is from about 600 m²/m³ to about 1500 m²/m³.
L. The catalyst of any one of Paragraphs A-K, wherein the geometric surface area per packed bed volume of the catalyst is from about 800 m²/m³ to about 1300 m²/m³.
M. The catalyst of any one of Paragraphs A-L, wherein the void fraction of the catalyst is from about 35% to about 55%.
N. The catalyst of any one of Paragraphs A-M, wherein the catalyst is in a shape comprising at least one of cylindrical, spherical, tubular, polylobular, ring, star, saddle, fluted, or ridged.
O. The catalyst of any one of Paragraphs A-N, wherein with the exception of the catalytic layer, the support is substantially free of Pd, Au, and KOAc.
P. A method of making the catalyst of any one of Paragraphs A-O, the method comprising permeating a support material comprising an external surface with Pd and Au to provide a metal-containing layer disposed within the support material adjacent to the external surface; wherein
the support material comprises:
about 60 wt % to about 99 wt % silica; and
about 1.0 wt % to about 5.0 wt % alumina;
the metal-containing layer further comprises Pd and Au.
Q. The method of Paragraph P, wherein permeating the support material comprises contacting the support material with a salt solution comprising a salt of Pd, a salt of Au, or a mixture thereof.
R. The method of Paragraph Q, wherein subsequent to contacting with the salt solution, permeating the support material comprises contacting the support material with a basic solution.
S. The method of any one of Paragraphs P-R, further comprising a washing step subsequent to the permeating step.
T. The method of any one of Paragraphs P-S, further comprising drying the support material subsequent to the permeating step.
U. The method of Paragraph T, wherein drying subsequent to the permeating step occurs at a temperature from about 40° C. to about 250° C.
V. The method of any one of Paragraphs S-U, further comprising drying the support material subsequent to the washing step.
W. The method of Paragraph V, wherein drying subsequent to the washing step occurs at a temperature from about 40° C. to about 250° C.
X. The method of any one of Paragraphs P-W, further comprising exposing the metal-containing layer to a reducing agent.
Y. The method of Paragraph X, wherein the exposing step occurs at a temperature from about 15° C. to about 500° C.
Z. The method of any one of Paragraphs P-Y, wherein the method further comprises impregnating the metal-containing layer with KOAc.
AA. The method of Paragraph Z, wherein the impregnating step occurs before the exposing step.
AB. The method of Paragraph Z, wherein the impregnating step occurs after the exposing step.
AC. The method of any one of Paragraphs Z-AB, further comprising drying the support material subsequent to the impregnating step.
AD. A process comprising contacting a reactant gas with the catalyst of any one of Paragraphs A-O to produce vinyl acetate monomer; wherein the reactant gas comprises ethylene, acetic acid, and $O_2$.

Other embodiments are set forth in the following claims, along with the full scope of equivalents to which such claims are entitled.

What is claimed is:
1. A catalyst comprising:
a support comprising:
an external surface;
about 60 wt % to about 99 wt % silica; and
about 1.0 wt % to about 5.0 wt % alumina;
a catalytic layer disposed within the support adjacent to the external surface, where the catalytic layer further comprises Pd, Au, and potassium acetate (KOAc);
a Brunauer-Emmett-Teller surface area of about 130 m²/g to about 300 m²/g; and
a geometric surface area per packed bed volume from about 1200 m²/m³ to about 1500 m²/m³;
wherein the geometric surface area per packed bed volume is calculated according to Equation 3:

$$\frac{\text{External Surface}}{\text{Mass}} * \frac{\text{Mass}}{\text{Volume}} = \frac{\text{External Surface}}{\text{Volume}} \quad \text{Eq. 3}$$

wherein
the KOAc is from 90 kg/m³ to 150 kg/m³ of the catalyst.
2. The catalyst of claim 1, wherein the alumina is present in the catalyst from about 1.0 wt % to about 3.0 wt %, Pd is present in the catalyst is from about 3 g/L to about 15 g/L, and the Au is present in the catalyst is from about 0.9 g/L to about 7.0 g/L.

3. The catalyst of claim 1, wherein the mass ratio of Pd to Au is from about 3.5:1 to about 2.0:1.

4. The catalyst of claim 1, wherein the Brunauer-Emmett-Teller surface area of the catalyst is from about 200 m²/g to about 250 m²/g.

5. The catalyst of claim 1, wherein a void fraction of the catalyst is from about 35% to about 55%.

6. The catalyst of claim 1, wherein with the exception of the catalytic layer, the support is substantially free of Pd, Au, and KOAc.

7. The catalyst of claim 1, wherein the KOAc is from about 90 kg/m³ to about 130 kg/m³ of the catalyst and the catalytic layer has an average thickness from about 50 µm to about 150 µm.

8. A catalyst comprising:
  a support comprising:
    an external surface;
    about 60 wt % to about 99 wt % silica; and
    about 1.0 wt % to about 5.0 wt % alumina;
  a catalytic layer disposed within the support adjacent to the external surface, where the catalytic layer further comprises Pd, Au, and potassium acetate (KOAc), and where the catalytic layer has an average thickness from about 200 µm to about 500 µm;
  a Brunauer-Emmett-Teller surface area of about 130 m²/g to about 300 m²/g; and
  a geometric surface area per packed bed volume from about 1200 m²/m³ to about 1500 m²/m³, wherein the geometric surface area per packed bed volume is calculated according to Equation 3:

$$\frac{\text{External Surface}}{\text{Mass}} * \frac{\text{Mass}}{\text{Volume}} = \frac{\text{External Surface}}{\text{Volume}}. \quad \text{Eq. 3}$$

9. The catalyst of claim 8, wherein the KOAc is from about 65 kg/m³ to about 100 kg/m³ of the catalyst.

10. The catalyst of claim 8, wherein the alumina is present in the catalyst from about 1.0 wt % to about 3.0 wt %, Pd is present in the catalyst is from about 3 g/L to about 15 g/L, and the Au is present in the catalyst is from about 0.9 g/L to about 7.0 g/L.

11. The catalyst of claim 8, wherein the mass ratio of Pd to Au is from about 3.5:1 to about 2.0:1.

12. A catalyst comprising:
  a support comprising:
    an external surface;
    about 60 wt % to about 99 wt % silica; and
    about 1.0 wt % to about 5.0 wt % alumina;
  a catalytic layer disposed within the support adjacent to the external surface, where the catalytic layer further comprises Pd, Au, and potassium acetate (KOAc);
  a Brunauer-Emmett-Teller surface area of about 130 m²/g to about 300 m²/g; and
  a geometric surface area per packed bed volume from about 1200 m²/m³ to about 1500 m²/m³;
  wherein the geometric surface area per packed bed volume is calculated according to Equation 3:

$$\frac{\text{External Surface}}{\text{Mass}} * \frac{\text{Mass}}{\text{Volume}} = \frac{\text{External Surface}}{\text{Volume}} \quad \text{Eq. 3}$$

wherein
  the KOAc is from about 60 kg/m³ to about 100 kg/m³ of the catalyst; and
  the catalytic layer has an average thickness from about 200 µm to about 550 µm.

13. The catalyst of claim 12, wherein the alumina is present in the catalyst from about 1.0 wt % to about 3.0 wt %, Pd is present in the catalyst is from about 3 g/L to about 15 g/L, and the Au is present in the catalyst is from about 0.9 g/L to about 7.0 g/L.

14. The catalyst of claim 12, wherein the mass ratio of Pd to Au is from about 3.5:1 to about 2.0:1.

15. The catalyst of claim 12, wherein the Brunauer-Emmett-Teller surface area of the catalyst is from about 200 m²/g to about 250 m²/g.

\* \* \* \* \*